(12) United States Patent
Holm

(10) Patent No.: US 7,772,273 B2
(45) Date of Patent: Aug. 10, 2010

(54) STABILIZED ATORVASTATIN

(75) Inventor: Per Holm, Vanløse (DK)

(73) Assignee: LifeCycle Pharma A/S, Horsholm (DK)

( * ) Notice: Subject to any disclaimer, the term of this patent is extended or adjusted under 35 U.S.C. 154(b) by 227 days.

(21) Appl. No.: 11/673,270

(22) Filed: Feb. 9, 2007

(65) Prior Publication Data

US 2007/0190138 A1 Aug. 16, 2007

Related U.S. Application Data

(60) Provisional application No. 60/790,449, filed on Apr. 7, 2006.

(30) Foreign Application Priority Data

Feb. 10, 2006 (DK) ................................ 2006 00203

(51) Int. Cl.
*A01N 43/36* (2006.01)
(52) U.S. Cl. ........................ 514/423; 514/422
(58) Field of Classification Search ................. 514/423
See application file for complete search history.

(56) References Cited

U.S. PATENT DOCUMENTS

| | | | | |
|---|---|---|---|---|
| 5,273,995 A | * | 12/1993 | Roth ........................ 514/422 |
| 5,686,104 A | * | 11/1997 | Mills et al. .................. 424/451 |
| 6,126,971 A | | 10/2000 | Mills et al. | |
| 6,531,507 B1 | | 3/2003 | Pflaum et al. | |
| 6,558,659 B2 | * | 5/2003 | Fox et al. ................. 424/78.31 |
| 7,030,151 B2 | | 4/2006 | Kerc et al. | |
| 2004/0138290 A1 | * | 7/2004 | Kerc et al. .................. 514/423 |

FOREIGN PATENT DOCUMENTS

| | | |
|---|---|---|
| WO | WO-0195939 | 12/2001 |
| WO | 02072073 | 9/2002 |
| WO | 2004071403 | 8/2004 |
| WO | WO-2006/123358 | 11/2006 |

* cited by examiner

*Primary Examiner*—Sreeni Padmanabhan
*Assistant Examiner*—Timothy E Betton
(74) *Attorney, Agent, or Firm*—Blank Rome LLP

(57) ABSTRACT

A stable pharmaceutical composition for oral administration comprising atorvastatin and an amount of a pharmaceutically acceptable organic alkalizing compound capable of establishing a microenvironment for atorvastatin having a pH of at least about 5, for example 2-amino-2-(hydroxymethyl)-1,3-propanediol (trometamol).

11 Claims, No Drawings

STABILIZED ATORVASTATIN

FIELD OF THE INVENTION

The invention relates to a stable pharmaceutical composition comprising atorvastatin. More specifically, the invention relates to atorvastatin stabilized with an organic alkalizing compound, especially 2-amino-2-(hydroxymethyl)-1,3-propanediol.

BACKGROUND OF THE INVENTION

Atorvastatin is a synthetic lipid-lowering agent. Atorvastatin is an inhibitor of 3-hydroxy-3-methylglutaryl-coenzyme A (HMG-CoA) reductase. This enzyme catalyzes the conversion of HMG-CoA to mevalonate, an early and rate-limiting step in cholesterol biosynthesis. Atorvastatin is useful for example as the calcium salt, i.e. [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, calcium salt (2:1) trihydrate. The molecular weight of atorvastatin calcium is 1209.42. Atorvastatin calcium is a white to off-white crystalline powder that is insoluble in aqueous solutions of pH 4 and below. Atorvastatin calcium is very slightly soluble in distilled water, pH 7.4 phosphate buffer, and acetonitrile, slightly soluble in ethanol, and freely soluble in methanol. However, atorvastatin is also useful as the magnesium salt. The atorvastatin salts may be either in crystalline form or in amorphous form or in a mixture of crystalline and amorphous form.

Atorvastatin is rapidly absorbed after oral administration; maximum plasma concentrations occur within 1 to 2 hours. Extent of absorption increases in proportion to atorvastatin dose. The absolute bioavailability of atorvastatin (parent drug) is approximately 14% and the systemic availability of HMG-CoA reductase inhibitory activity is approximately 30%. The low systemic availability is attributed to presystemic clearance in gastrointestinal mucosa and/or hepatic first-pass metabolism. Although food decreases the rate and extent of drug absorption by approximately 25% and 9%, respectively, as assessed by Cmax and AUC, LDL-C reduction is said to be similar whether atorvastatin is given with or without food. Plasma atorvastatin concentrations are lower (approximately 30% for Cmax and AUC) following evening drug administration compared with morning. However, LDL-C reduction is said to be the same regardless of the time of day of drug administration It is well-known that statins are pharmacologically active in the hydroxy acid form, whereas the corresponding lactone form may be considered a pro-drug which may convert to the active hydroxy acid in vivo. Atorvastatin is conveniently applied in drug composition as a salt of the pharmacologically active hydroxy acid form.

The atorvastatin hydroxy acid form-lactone form equilibrium and inter-conversion kinetics is pH highly dependent. The acid-catalyzed reaction is reversible, whereas the base-catalyzed reaction is practically irreversible: At pH>6, the equilibrium reaction is not detectable and greatly favors the hydroxy acid form (Kearney et al., *Pharmaceutical Research*, 1993, vol. 10, no. 10, p. 1461-65).

Accordingly, it is advisable to establish a near-neutral or basic microenvironment for atorvastatin in the pharmaceutical composition in order to stabilize the equilibrium, i.e. avoid presence of the inactive lactone form, for example a microenvironment having a pH above about 5 or even a pH above about 6.

WO 2006/123358 discloses a pharmaceutical composition comprising atorvastatin and a carrier comprising about 0.5% to about 3.0% by weight of tromethamine and an additional stabilizer such as an antioxidant.

U.S. Pat. No. 6,126,971 disclose the use of a pharmaceutically acceptable inorganic alkalizing compound as a stabilizer in a pharmaceutical composition comprising atorvastatin. Such inorganic alkalizing compounds are typically conventional basic salts of metals or alkaline earth metals. Typically, calcium carbonate is used for this purpose. However, in order to achieve the desired effect, a considerable amount of calcium carbonate is necessary, typically from about 5% w/w to about 75% w/w.

Such a high amount of calcium carbonate in a pharmaceutical composition creates vast problems in preparing tablets (solid dosage forms).

Accordingly, there is an unmet need for a stable atorvastatin-containing composition which can easily be processed into tablets.

SUMMARY OF THE INVENTION

Surprisingly, the inventor has now found that the amount of stabilizer can be significantly removed by using a pharmaceutically acceptable organic alkalizing compound. By using this compound, the amount of stabilizer can be significantly reduced, and the hitherto known problems in tablet production can be avoided.

Accordingly, the present invention relates to a pharmaceutical composition for peroral treatment of hypercholesterolemia and/or hyperlipidemia comprising a pharmaceutically acceptable salt of atorvastatin (2-(4-fluorophenyl)-β,δ-dihydroxy-5-(1-methylethyl)-3-phenyl-4-[(phenylamino)carbonyl]-1H-pyrrole-1-heptanoic acid) and a pharmaceutically acceptable organic alkalizing compound in an amount of less than 5% w/w of the composition, preferably below 1% w/w of the composition, more preferably at or below 0.5% w/w, without the presence of further stabilizers in the composition.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges also encompassed with the invention, subject to any specifically excluded limit in the stated range. Where the stated range includes on or both of these limits, ranges excluding either one or both of those included limits are also included in the invention.

Unless defined otherwise, all technical and scientific terms used herein have the same meaning as commonly understood by one or ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an" and "the" include plural references unless the context clearly dictates otherwise.

The atorvastatin is crystalline atorvastatin calcium, amorphous atorvastatin calcium, crystalline atorvastatin magnesium, amorphous atorvastatin magnesium, a mixture of amorphous and crystalline atorvastatin calcium and a mixture of amorphous and crystalline atorvastatin magnesium. In a preferred embodiment, the atorvastatin is the hemi-calcium salt or the magnesium salt, in crystalline or amorphous form, but any pharmaceutically acceptable salt can be used. In a most preferred embodiment of the invention, atorvastatin is used in the crystalline magnesium salt form.

A basic or near-neutral micro-environment for atorvastatin, i.e. a micro-environment for atorvastatin of at least about pH 5, preferably at least about pH 6, can be established by incorporating one or more other pharmaceutically acceptable organic alkalizing compounds into the pharmaceutical composition, in particular amines, amides and ammonium compounds being very soluble in water, for example compounds exhibiting a water solubility of at least 100 mg/mL at 25° C., preferably at least 200 mg/mL, even more preferably at least 300 mg/mL, especially at least 500 mg/mL.

Specific examples of compounds that may be useful are ammonia, ammonium lactate, ammonium bicarbonate, ammonium hydroxide, ammonium phosphate dibasic, mono ethanolamine, di ethanolamine, tri ethanolamine, tri hydroxymethylaminomethane, ethylenediamine, N-methyl glucamide, 6N-methyl glucamine, meglucamine and L-lysine.

A preferred compound is tromethamine (IUPAC name: 2-amino-2-(hydroxymethyl)-1,3-propanediol; also known as tris buffer, tham, trometamol, trisaminol or trisamine). Trometamol has a water solubility of about 550 mg/mL at 25° C.

Tromethamine is useful in an amount of below 5% w/w of the pharmaceutical composition, preferably below 4% w/w, more preferably below 3% w/w, even more preferably below 2% w/w. Typically, tromethamine is used in the pharmaceutical composition comprising atorvastatin in an amount of at the most about 1% w/w of the composition. In a preferred embodiment of the invention, tromethamine is used in an amount of below 1% w/w of the invention, preferably below 0.8% w/w, more preferably below 0.7% w/w, even more preferably below about 0.6% w/w, such as below about 0.5% w/w, of the composition. It has been shown in the Examples herein that even an amount of tromethamine as low as about 0.1% w/w is useful for preventing formation of atorvastatin in the undesirable lactone form. Tromethamine should be present in the atorvastatin composition in an amount of at least above 0.01% w/w. In a preferred embodiment of the invention, the atorvastatin composition comprises from about 0.02% w/w to about 1.0% w/w of tromethamine.

When using tromethamine in the amounts specified herein, an atorvastatin composition is stabilized to the extent that the content of atorvastatin lactone is essentially unchanged throughout the shelf-life of the composition. More specifically, the stable atorvastatin composition comprises less than 0.2% w/w of atorvastatin lactone after 6 months storage at 25° C. at 60% relative humidity.

The pharmaceutical atorvastatin composition may be in the form of granulate, granules, grains, beads or pellets, which are mixed and filled into capsules or sachets or are compressed to tablets by conventional methods. The granulate, granules, grains, beads or pellets are optionally entero-coated or coated with a protective coating.

As shown in the Examples herein, there is no need for any additional stabilizing compound, neither an antioxidant nor any other stabilizer. In a preferred embodiment of this invention, the composition is essentially free of antioxidants or any other stabilizing compounds than the organic alkalizing compound capable of establishing a micro-environment for atorvastatin of pH at least 5.

In the present context the term "pharmaceutically acceptable excipient" is intended to denote any material, which is inert in the sense that it substantially does not have any therapeutic and/or prophylacetic effect per se. Such excipients may be added with the purpose of making it possible to obtain a pharmaceutical, cosmetic and/or foodstuff composition, which have acceptable technical properties. The pharmaceutical composition of the invention may contain one or more pharmaceutically acceptable excipients.

Examples of suitable excipients for use in a composition or solid dosage form according to the invention include fillers, diluents, disintegrants, binders, stabilizers, lubricants etc. or mixtures thereof. As the composition or solid dosage form according to the invention may be used for different purposes, the choice of excipients is normally made taken such different uses into considerations. Other pharmaceutically acceptable excipients for suitable use are e.g. acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include lactose (e.g. spray-dried lactose, a-lactose, b-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g., Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol (e.g. Pearlitol 50C), dextrins, maltodextrins, starches or modified starches (including potato starch, maize starch and rice starch), calcium phosphate (e.g., basic calcium phosphate, calcium hydrogen phosphate, dicalcium phosphate hydrate), calcium sulfate, calcium carbonate, sodium alginate, collagen etc.

Specific examples of diluents are e.g., calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium (Ac-di-sol), crospovidone, polacrillin potassium, sodium starch glycolate, starch, pregelatinized starch, carboxymethyl starch (e.g. Primogel® and Explotab®) etc.

Specific examples of binders are e.g., acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the first or, preferably, the second (statin-containing) composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g., flavoring agents, coloring agents, taste-masking agents, pH-adjusting agents, buffering agents, preservatives, stabilizing agents, anti-oxidants, wetting agents, humidity-adjusting agents, surface-active agents (e.g. Polysorbate 80/Tween 80), suspending agents, absorption enhancing agents, agents for modified release etc.

A composition or solid dosage form according to the invention may also include one or more surfactants or substances having surface-active properties. It is contemplated that such substances are involved in the wetting of the slightly soluble active substance and thus, contributes to improved solubility characteristics of the active substance. Suitable surfactants for use in a composition or a solid dosage form according to the invention are surfactants such as, e.g., hydrophobic and/or hydrophilic surfactants as those disclosed in WO 00/50007 in the name of Lipocine, Inc.

Specific examples of suitable surfactants are polyethoxylated fatty acids such as, e.g., fatty acid mono- or diesters of polyethylene glycol or mixtures thereof such as, e.g., mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, polyethylene glycol glycerol fatty acid esters, i.e. esters like the above-mentioned but in the form of glyceryl esters of the individual fatty acids; glycerol, propylene glycol, ethylene glycol, PEG or sorbitol esters with e.g., vegetable oils like e.g., hydrogenated castor oil, almond oil, palm kernel oil, castor oil, apricot kernel oil, olive oil, peanut oil, hydrogenated palm kernel oil and the like, polyglycerized fatty acids like e.g., polyglycerol stearate, polyglycerol oleate, polyglycerol ricinoleate, polyglycerol linoleate, propylene glycol fatty acid esters such as, e.g., propylene glycol monolaurate, propylene glycol ricinoleate and the like, mono- and diglycerides like e.g. glyceryl monooleate, glyceryl dioleae, glyceryl mono- and/or dioleate, glyceryl caprylate, glyceryl caprate etc.; sterol and sterol derivatives; polyethylene glycol sorbitan fatty acid esters (PEG-sorbitan fatty acid esters) such as esters of PEG with the various molecular weights indicated above, and the various Tween® series (from ICI America, Inc.); polyethylene glycol alkyl ethers such as, e.g., PEG oleyl ether and PEG lauryl ether; sugar esters like e.g. sucrose monopalmitate and sucrose monolaurate; polyethylene glycol alkyl phenols like e.g. the Triton® X or N series (Union Carbide Chemicals & Plastics Technology Corporation); polyoxyethylene-polyoxypropylene block copolymers such as, e.g., the Pluronic® series from BASF Aktiengesellschaft, the Synperonic® series from ICI America, Inc., Emkalyx, Lutrol® from BASF Aktiengesellschaft, Supronic etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407; sorbitan fatty acid esters like the Span® series (from ICI) or Arlacel® series (from ICI) such as, e.g., sorbitan monolaurate, sorbitan monopalmitate, sorbitan monooleate, sorbitan monostearate etc.; lower alcohol fatty acid esters like e.g., oleate, isopropyl myristate, isopropyl palmitate etc.; ionic surfactants including cationic, anionic and zwitterionic surfactants such as, e.g., fatty acid salts, bile salts, phospholipids, phosphoric acid esters, carboxylates, sulfates and sulfonates etc.

When a surfactant or a mixture of surfactants is present in a composition of the invention, the concentration of the surfactant(s) is normally in a range of from about 0.1-80% w/w such as, e.g., from about 0.1 to about 20% w/w, from about 0.1 to about 15% w/w, from about 0.5 to about 10% w/w, or alternatively, from about 0.10 to about 80% W/w such as, e.g. from about 10 to about 70% w/w, from about 20 to about 60% w/w or from about 30 to about 50% w/w.

Examples of film polymers include water soluble agents such as hydroxypropyl-methylcellulose, Metolose® (HPMC), hydroxypropylmethylcellulose, Klucel® (HPC), polyvinyl alcohol (PVA), polyvinylpyrrolidone (PVP) or combinations of PVA and PVP (Kollicoat® IR) and acid soluble acrylic polymer (Eudragit E, soluble in gastric juice).

Wetting and pH adjusting agent might be included in the coating suspension.

Coating of the atorvastatin composition is performed in conventional coating equipment such as drum coater, perforated vessel or fluidized bed (Wurster insert).

The composition of the invention may be prepared by any method suitable for incorporation of poorly water-soluble active substances. The pharmaceutical compositions may be prepared by any convenient method such as, e.g. granulation, mixing, spray drying etc. Conventional wet granulation processes are preferred.

The pharmaceutical composition of the invention may be process into a solid dosage form which may be a single unit dosage form or in the form of a polydepot dosage form containing a multiplicity of individual units such as pellets, beads and/or granules.

Usually, the pharmaceutical composition of the invention is intended for administration via the oral, buccal or sublingual administration route.

The invention also relates to the above-mentioned presentation form. Within the scope of the invention are compositions/solid dosage forms that are intended to release the active substance in a fast release, a delayed release or modified release manner.

A useful solid dosage form comprises a pharmaceutical composition in particulate form as described above. The details and particulars disclosed under this main aspect of the invention apply mutatis mutandis to the other aspects of the invention. Accordingly, the properties with respect to increase in bioavailability, therapeutic and/or pharmacological response, changes in bioavailability parameters, reduction in adverse food effect as well as release of one or more fibrates etc. described and/or claimed herein for pharmaceutical compositions in particulate form are analogues for a solid dosage form according to the present invention.

The solid dosage form, i.e. in unit dosage form, comprises from about 5 to about 80 mg of atorvastatin statin or the corresponding amount of a pharmaceutically acceptable salt thereof, for example 5 mg og 10 mg or 20 mg or 40 mg or 80 mg of atorvastatin or the corresponding amount of a pharmaceutically acceptable salt thereof.

A tablet containing the pharmaceutical composition of to the invention may also be coated in order to obtain suitable properties e.g. with respect to release of the active substance. The coating may be applied on single unit dosage forms (e.g. tablets, capsules) or it may be applied on a polydepot dosage form or on its individual units.

Suitable coating materials are e.g. methylcellulose, hydroxypropylmethyl-cellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, zein.

Plasticizers and other ingredients may be added in the coating material. The same or different active substance may also be added in the coating material.

Materials and Methods

Materials

The materials used for manufacturing of the atorvastatin granule, blend and coating are:

| Substance | Function | Trade name |
|---|---|---|
| Atorvastatin magnesium, crystalline | Active drug | Atorvastatin Mg, cryst. |
| Mannitol | Filler | Pearlitol ® 50 C |
| Microcrystalline cellulose | Filler | Avicel ® 101 |
| Hydroxypropyl cellulose | Binder | Klucel ® EXF |
| Polysorbate 80 | Wetting agent | Tween ® 80 |
| Tromethamine/Trometamol | Alkalizing agent | Tris Amino Buffer |
| Microcrystalline cellulose | Filler | Avicel ® 200 |
| Magnesium Stearate | Lubricant | LIGA ® Mg stearate MF-2-V |
| Opadry II White 45F28595 | Film | Opadry II |

Tablets, capsules or granules may be enteric coated with different types of polymers such as hydroxypropylmethylcellulose acetate succinate (Aqoat), cellulose acetate phthalate CAP, hydroxypropylmethylcellulose phtalate HPMCP or methacrylic acid copolymers such as Eudragit L30D, Eudragit 100/S, Eudragit 100/L.

Equipment

Process equipment used for manufacturing atorvastatin granule and fenofibrate and atorvastatin bi-layer tablets:

| | |
|---|---|
| Mixer | Blade Mixer Herdolph RZR |
| High Shear mixer | PMA 65 |
| Milling/sieving equipment | 8 mm mesh (wet sieving); 1.6 mm mesh (dry sieving) |
| Fluid bed | MP 2/3 |
| Tablet press | Double sided Fette 3090 rotary tablet machine |
| Punches | Oblong 18 × 7 R6.5 mm |
| Coater | GMPC III |

Methods

Atorvastatin Granulation

A binder solution containing tromethamine was prepared by dissolving polysorbate 80 in hot purified water at 90° C. The solution was cooled to room temperature. The mixture was stirred and hydroxypropylcellulose was added under stirring. Tromethamine was dissolved in the binder solution shortly before each granulation.

Mannitol was sieved through 1.5 mm round sieve. The dry ingredients, i.e. atorvastatin magnesium (crystalline), microcrystalline cellulose, mannitol and hydroxypropylcellulose, were pre-mixed for 2 minutes in a high shear mixer PMA.

The binder solution was added to the granule using a pressure nozzle and a homogeneous distribution of binder solution in the granule was obtained.

Blending Atorvastatin Granule with Extragranular Excipients

The high shear granule was mixed with microcrystalline cellulose (Avicel PH200), magnesium stearate was added and blended for 2 min (stirring).

Tablet Coating

A coating suspension was prepared by suspending Opadry II in purified water. The tablets were loaded into the coater and preheated to 40° C. before spraying. The suspension was sprayed onto the tablets to obtain a weight gain of 3%.

Test for Impurities

Sample Preparation for Atorvastatin:

10 tablets were grounded and about 963 mg±10 mg of grounded tablet material was placed in a 25 mL volumetric flask. 5 mL of water and 15 ml acetonitrile was added and the mixture was stirred on a magnetic stirrer for 60 minutes. Acetonitrile was added up to a total volume of 25 mL and filtrated through 0.45 μm filter. The sample is diluted ×25 for quantification. Both concentrated and diluted sample was injected into the HPLC system HPLC:

The sample was subjected to HPLC analysis on a Shimadzu 2010A with auto sampler cooling and dual wavelength UV detector.

Eluent A: 10.6 mM formic acid (in water). Eluent B: 10.6 mM formic acid (in acetonitrile).
Column: varian Pursuit C18 3 micro, 150×3.0 mm
Oven temperature: 30° C.
Injection volume: 15 microliter
Flow: 0.5 mL/min
Gradient:

| Time (min) | Eluent A | Eluent B |
|---|---|---|
| 0.0 | 60 | 40 |
| 0.5 | 60 | 40 |
| 30.0 | 15 | 85 |
| 35.0 | 60 | 40 |
| 40.0 | 60 | 40 |

Detection wavelength—fenofibrate: 295 nm
Detection wavelength—atorvastatin: 240 nm This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

EXAMPLE 1

Preparation of Atorvastatin Granulate

The following atorvastatin granulate denoted 1A was prepared in a conventional manner using wet granulation, i.e. mixing atorvastatin, lactose (carrier) and calcium carbonate (stabilizer disclosed in U.S. Pat. No. 6,126,971), adding the appropriate amount of hydroxypropyl cellulose (Klucel; binder) and natrium carboxymethyl cellulose (Ac-di-sol; disintegrant), adding sterile water to the mixture, mixing and drying off the water, sifting the dried mixture and adding magnesium stearate (lubricant) and microcrystalline cellulose (Avicel).

The following atorvastatin granulate denoted 1B was prepared in a conventional manner using wet granulation: A binder solution is prepared by dissolving hydroxypropyl cellulose (binder) and trometamol (stabilizer) in water (surfactant may be added, e.g. Polysorbat 80). Atorvastatin, mannitol (carrier), hydroxypropyl cellulose (binder) and microcrystalline cellulose (Avicel; filler) is transferred to a high shear mixer. The dry ingredients are premixed for 2 minutes, followed by addition of the binder solution at 150 rpm (impeller) and 2000 rpm (chopper) to form a wet mass. Water is added and the mixture is mixed for 2 minutes, resulting in granule formation. The wet granulate is sieved (1.0 mm round opening) and dried in a fluid bed. The dry granulate is sieved (1.0 mm round opening).

'%' denotes percentage of granulate.

'mg/tablet' denotes the amounts present in the pharmaceutical composition of the invention in a single solid dosage form (a tablet):

| Substance | Ingredient | 1A % | 1A mg/tablet | 1B % | 1B mg/tablet |
|---|---|---|---|---|---|
| Drug | Atorvastatin magnesium | 5.3 | 10.9 | 14.6 | 44 |
| Carrier | Lactose 200 mesh | 16.1 | 32.8 | — | — |
|  | Mannitol (Pearlitol 50C) | — | — | 41 | 122 |
| Excipients | Magnesium stearate | 0.5 | 1.00 | 0.5 | 1.5 |
|  | Ac-di-sol | 5.0 | 10.2 | — | — |
|  | Calcium carbonate | 16.2 | 33.0 | — | — |
|  | Klucel | 1.5 | 3.0 | 2.4 | 7 |
|  | Polysorbate 80 | 0.4 | 0.6 | 0.8 | 2.4 |
|  | Avicel | 55.0 | 111.7 | 40 | 119 |
|  | Trometamol | — | — | 0.8 | 2.5 |

EXAMPLE 2

Tablet—Atorvastatin and Fenofibrate Combination Tablet (Two-Layer Tablet)

A two-layer tablet denoted 4E was prepared in a conventional manner in a Fette 3090 tablet machine using a fenofibrate granulate prepared as disclosed in WO2005/034920 and WO 2006/084475 and the atorvastatin granulate composition 1B of example 1, the resulting tablet having a weight of about 1060 mg.

A two-layer tablet denoted 4B was prepared in a conventional manner in a Fette 3090 tablet machine using a fenofibrate granulate prepared as disclosed in WO2005/034920 and WO 2006/084475 and atorvastatin granulate 1B of example 1, the resulting tablet having a weight of about 930 mg.

EXAMPLE 3

Stability of Pharmaceutical Composition of the Invention (Atorvastatin)

Stability of the fenofibrate and atorvastatin combination two-layer tablets prepared according to the invention (example 2, tablet 4B—but varying amounts of trometamol stabilizer was added) was measured as described above (test for presence of atorvastatin in lactone form) after 1 month storage at 40° C. and 75% RH.

Results are shown below.

|  | Trometamole added | | |
|---|---|---|---|
|  | 1% w/w | 2% w/w | 5% w/w |
| Lactone content | <0.05% | <0.05% | <0.05% |

EXAMPLE 4

Tablet—Atorvastatin and Fenofibrate Combination Tablet (Two-Layer Tablet)

The following atorvastatin granules and blends and combination tablets were prepared as described in Methods and in Example 2:

| Components | w/w % granule TABLET 4-I | w/w % tablet TABLET 4-I | w/w % granule TABLET 4-II | w/w % tablet TABLET 4-II | w/w % granule TABLET 4-III | w/w % tablet TABLET 4-III |
|---|---|---|---|---|---|---|
| Atorvastatin blend | | | | | | |
| Atorvastatin magnesium crystalline | 19.0 | 5.02 | 9.51 | 2.51 | 4.8 | 1.26 |
| Mannitol | 58.2 | 15 | 68.4 | 18 | 73.3 | 19 |
| Microcrystalline cellulose (Avicel PH 101) | 20 | 5.3 | 20 | 5.3 | 20 | 5.3 |
| Microcrystalline cellulose (Avicel PH 200) |  | 8.6 |  | 8.6 |  | 8.6 |
| Hydroxypropylcellulose | 1.2 | 0.32 | 1.2 | 0.32 | 1.2 | 0.32 |
| Polysorbate 80 | 1.1 | 0.29 | 0.5 | 0.15 | 0.3 | 0.07 |
| Magnesium stearate |  | 0.18 |  | 0.18 |  | 0.18 |
| Tromethamine/Trometamol | 0.5 | 0.13 | 0.5 | 0.13 | 0.5 | 0.13 |
| Fenofibrat blend | | | | | | |
| Fenofibrate |  | 11.7 |  | 11.7 |  | 11.7 |
| Lactose monohydrate |  | 28 |  | 28 |  | 28 |
| Polyethylenglycol, 6000 |  | 15 |  | 15 |  | 15 |
| Poloxamer 188 |  | 6.5 |  | 6.5 |  | 6.5 |
| Magnesium stearate |  | 0.62 |  | 0.62 |  | 0.62 |

-continued

| Components | w/w % granule TABLET 4-I | w/w % tablet TABLET 4-I | w/w % granule TABLET 4-II | w/w % tablet TABLET 4-II | w/w % granule TABLET 4-III | w/w % tablet TABLET 4-III |
|---|---|---|---|---|---|---|
| Coating | | | | | | |
| Opadry II White 45F28595 (Polydextrose, HPMC, PEG and titan dioxide) | | 3.0 | | 3.0 | | 3.0 |

Stability of TABLET 4-III was measured as described above (test for presence of atorvastatin in lactone form) after 3 and 6 month storage at 5° C., 25° C./60% RH and 30° C./55% RH, respectively:

Content of lactone (w/w %):

| | 5 | 25/60 | 30/65 |
|---|---|---|---|
| 0 months | 0.13 | 0.13 | 0.13 |
| 3 months | 0.17 | 0.15 | — |
| 6 month | 0.10 | 0.10 | 0.13 |

The lactone content is essentially unchanged, i.e. the atorvastatin is stabilized.

EXAMPLE 5

Amount of Stabilizer—I

The stability of combination tablets 4-III of example 4 with 0.5% and 1.0% of tromethamine in the atorvastatin granule, respectively, was investigated with regard to formation of the lactone.

The results from accelerated stability testing are shown below.

| | | 1 month | | 3 months | | 6 months | |
|---|---|---|---|---|---|---|---|
| Formulation - TABLET 4-III | Start 25° C. | 25° C./ 60% RH | 40° C./ 75% RH | 25° C./ 60% RH | 40° C./ 75% RH | 25° C./ 60% RH | 40° C./ 75% RH |
| 0.5% tromethamine | 0.14% | 0.11% | 0.14% | 0.13% | 0.49% | 0.14% | 0.35% |
| 1.0% tromethamine | 0.09% | 0.11% | 0.16% | 0.1% | 0.22% | 0.1% | 0.29% |

The results show that tablets containing 1% tromethamine in the atorvastatin granule does not reduce the lactone level significantly compared to the tablets containing 0.5% tromethamine in atorvastatin granule. A level of 0.5% tromethamine in the atorvastatin granule is considered sufficient for neutralizing acid moieties in the granule.

EXAMPLE 6

Amount of Stabilizer—II

The influence of adding 0%, 0.02%, 0.1%, 0.5%, 1% (high and normal humidity), 2% and 5% of tromethamine, respectively, to an atorvastatin granule prepared according to Example 1B was investigated.

The results from accelerated stability testing are shown below (Effect of varying the tromethamine concentration in the atorvastatin granule on the lactone formation in combination tablets 4-III of example 4 stored for 1 month at 40° C./75% relative humidity (RH).

| Tromethamine, % by weight | % lactone after 1 month at 40° C./75% RH |
|---|---|
| 0 | 0.07 |
| 0.02 | 0.05 |
| 0.1 | 0.03 |
| 0.5 | 0.04 |
| 1.0 | 0.02 |
| 2 | 0.02 |
| 5 | 0.01 |

The results show that addition of tromethamine reduces the formation of the lactone impurity. However, increasing the amount of tromethamine from 1% to 2% and 5% did not reduce the lactone formation further, whereas addition of 0.5%, 0.1% and 0.02% caused only a slightly less improvement in stability. Thus, an atorvastatin formulation can be adequately stabilized with an amount of tromethamine of below 0.5% by weight.

The specific embodiments herein disclosed are intended as illustrations of several aspects of the invention. Any equivalent embodiments are intended to be within the scope of this invention. Indeed, various modifications of the invention in addition to those shown and described herein will become apparent to those skilled in the art form the foregoing description. Such modifications are also intended to fall within the scope of the appended claims.

Various references are cited herein, the disclosures of which are incorporated by reference in their entireties.

The invention claimed is:

1. A stable pharmaceutical composition for oral administration comprising atorvastatin or a pharmaceutically acceptable salt thereof and an amount of a pharmaceutically acceptable organic alkalizing compound capable of establishing a micro-environment for atorvastatin having a pH of at least about 5, wherein the composition is free of other stabilizing compounds, the organic alkalizing compound is present in an amount ranging from 0.01 to 0.5% w/w, and the composition comprises less than 0.2% w/w of atorvastatin lactone after 6 months storage at 25° C. at 60% relative humidity.

2. The pharmaceutical composition according to claim 1, wherein the organic alkalizing compound is selected from the group consisting of amines, amides and ammonium compounds.

3. The pharmaceutical composition according to claim 1, wherein the alkalizing compound is selected from the group consisting of ammonium lactate, ammonium bicarbonate, mono ethanolamine, di ethanolamine, tri ethanolamine, tri hydroxymethylaminomethane, ethylenediamine, N-methyl glucamide, 6N-methyl glucamine, meglucamine, L-lysine and 2-amino-2-(hydroxymethyl)-1,3-propanediol.

4. The pharmaceutical composition according to claim 1, wherein the alkalizing compound is 2-amino-2-(hydroxymethyl)-1,3-propanediol (tromethamine).

5. The pharmaceutical composition according to claim 1, which is free of antioxidants.

6. The pharmaceutical composition according to claim 4, comprising from 0.02% w/w to 1.0% w/w of tromethamine.

7. The pharmaceutical composition according to claim 4, comprising tromethamine in an amount below 0.5% w/w.

8. The pharmaceutical composition according to claim 1, wherein the atorvastatin is selected from the group consisting of crystalline atorvastatin calcium, amorphous atorvastatin calcium, crystalline atorvastatin magnesium, amorphous atorvastatin magnesium, a mixture of amorphous and crystalline atorvastatin calcium and a mixture of amorphous and crystalline atorvastatin magnesium.

9. The pharmaceutical composition according to claim 1, wherein the atorvastatin is crystalline atorvastatin magnesium.

10. A tablet comprising atorvastatin or a pharmaceutically acceptable salt thereof and tromethamine, wherein the tablet is free of other stabilizing compounds, and the tablet comprises less than 0.5% w/w of tromethamine and less than 0.2% w/w of atorvastatin lactone after 6 months storage at 25° C. at 60% relative humidity.

11. A method for preparing a tablet comprising atorvastatin and an amount of a pharmaceutically acceptable organic alkalizing compound capable of establishing a microenvironment for atorvastatin having a pH of at least about 5, which method comprises the steps of:
   i) preparing a solid pharmaceutical composition by wet granulation of atorvastatin and the alkalizing compound, and
   iii) compressing the composition into a tablet, wherein the composition is free of other stabilizing compounds.

* * * * *